United States Patent [19]

Tice

[11] Patent Number: 5,378,678
[45] Date of Patent: Jan. 3, 1995

[54] 2-ARYL-5,6-RING-FUSED PYRIMIDINES AND HERBICIDAL USE

[75] Inventor: Colin M. Tice, Melrose Park, Pa.

[73] Assignee: Rohm and Haas Company, Philadelphia, Pa.

[21] Appl. No.: 128,326

[22] Filed: Sep. 28, 1993

Related U.S. Application Data

[63] Continuation of Ser. No. 916,780, Jul. 17, 1992, abandoned.

[51] Int. Cl.$^6$ .................... A01N 43/54; C07D 239/70
[52] U.S. Cl. ...................................... 504/242; 504/240; 544/278; 544/284; 544/287
[58] Field of Search ................. 544/278, 284, 287; 504/240, 242

[56] References Cited

U.S. PATENT DOCUMENTS

| | | | |
|---|---|---|---|
| 3,748,327 | 7/1983 | Beyerle et al. | 544/284 |
| 4,431,440 | 2/1984 | Bhalla et al. | 544/289 |
| 4,746,352 | 5/1988 | Wenger et al. | 504/240 |
| 5,266,554 | 11/1993 | Suchy et al. | 504/240 |
| 5,300,477 | 4/1994 | Tice | 504/242 |

OTHER PUBLICATIONS

Kronberg, L. et al., "Studies on the medicinal chemistry of oxoquinazolines" Acta. Pharm. Sueica 7 1970, pp. 37–46.

Bogentoft, C. et al., "Studies on the medicinal chemistry of oxoquinalzolines" Acta. Pharm. Sueica 6 1969, pp. 489–500.

*Primary Examiner*—Mukund J. Shah
*Assistant Examiner*—Pavanaram K. Sripada
*Attorney, Agent, or Firm*—Clark R. Carpenter; Joseph F. Leightner; Thomas D. Rogerson

[57] ABSTRACT

A class of 2-aryl-5,6-ring-fused pyrimidines which is useful in the control of weeds is of the general formula:

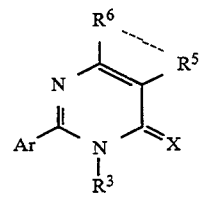

wherein Ar is an optionally substituted aromatic or heteroaromatic ring; $R^3$ is an alkynyl or alkoxyalkyl group, $-R^5--R^6-$ is a fused ring moiety bonded to the pyrimidine ring at the 5 and 6 positions; and X is oxygen or sulfur.

12 Claims, No Drawings

2-ARYL-5,6-RING-FUSED PYRIMIDINES AND HERBICIDAL USE

This application is a continuation of application Ser. No. 916,780 filed Jul. 17, 1992, now abandoned.

BACKGROUND OF THE INVENTION

A need continues for novel and improved herbicidal compounds and compositions. This is particularly so since the targets of herbicides can become resistant to known herbicides over time and after use of such compositions. Additionally, economic and environmental considerations can favor herbicides having different modes of performance than those currently used. This invention relates to novel 2-aryl-5,6-ring-fused pyrimidines and their use as broad spectrum herbicides.

SUMMARY OF THE INVENTION

2-Aryl-5,6-ring-fused pyrimidines which are useful in the control of weeds have been discovered. These compounds are of the general formula:

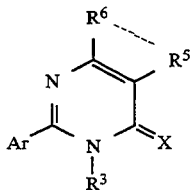

I wherein Ar is a substituted or unsubstituted aryl or heteroaromatic group; $R^3$ is an alkynyl or alkoxyalkyl group; and -$R^5$- - - $R^6$- is a fused ring moiety bonded to the pyrimidine ring at the 5 and 6 positions. This invention also teaches methods of preparing these compounds as well as methods of using the compounds as herbicides

EMBODIMENTS OF THE INVENTION

Compound Embodiments

An embodiment of the present invention are compounds of the general formula:

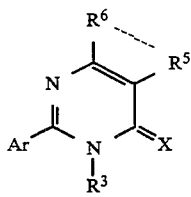

I wherein Ar is a substituted or unsubstituted aryl or heteroaromatic group (e.g. aromatic ring structure having 4 to 10 carbon atoms); $R^3$ is an alkynyl or alkoxyalkyl group; -$R^5$- - - $R^6$- is a fused ring moiety bonded to the pyrimidine ring at the 5 and 6 positions, that is, -$R^5$- - - $R^6$- together with the carbon atoms to which it is attached form a ring bonded to the pyrimidine ring; and X is oxygen or sulfur.

Ar is an aryl or heteroaromatic group, preferably furyl, phenyl, pyridyl, or thienyl, and may be optionally substituted with up to three substituents independently selected from bromo; chloro; fluoro; ($C_1$-$C_{12}$)alkyl, preferably($C_1$-$C_6$)alkyl; cyclo($C_3$-$C_8$)alkyl, preferably cyclo($C_5$-$C_6$)alkyl; ($C_2$-$C_{12}$)alkenyl, preferably ($C_2$-$C_6$)alkenyl; cyclo($C_3$-$C_8$)alkenyl; ($C_2$-$C_{12}$)alkynyl, preferably ($C_2$-$C_6$)alkynyl; halo($C_1$-$C_{12}$)alkyl, preferably halo($C_1$-$C_6$)alkyl; polyhalo($C_1$-$C_{12}$)alkyl, preferably polyhalo($C_1$-$C_6$)alkyl; halo($C_2$-$C_{12}$)alkenyl, preferably halo($C_2$-$C_6$)alkenyl; polyhalo($C_2$-$C_{12}$)alkenyl, preferably polyhalo($C_2$-$C_6$)alkenyl; halo($C_2$-$C_6$)alkynyl; polyhalo($C_2$-$C_6$)alkynyl; ($C_1$-$C_{12}$)alkoxy, preferably ($C_1$-$C_6$)alkoxy; ($C_1$-$C_{12}$)alkylthio, preferably ($C_1$-$C_6$)alkylthio; ($C_1$-$C_{12}$)alkylsulfonyl; ($C_1$-$C_{12}$)alkylsulfinyl; phenyl; phen($C_1$-$C_{12}$)alkyl; phen($C_2$-$C_{12}$)alkenyl; phen($C_2$-$C_{12}$)alkynyl; cyano; halo($C_1$-$C_{12}$)alkoxy, preferably halo($C_1$-$C_6$)alkoxy; carbo($C_1$-$C_6$)alkoxy; and nitro. Substituent groups can be branched or unbranched. Preferred phenyl groups are phenyl, 3-methylphenyl, 3-methoxyphenyl, 3-nitrophenyl, 3-trifluoromethylphenyl, 3-bromophenyl, 3-chlorophenyl, 4-chlorophenyl, 3,5-dichlorophenyl, 2-fluorophenyl, 3-fluorophenyl, 4-fluorophenyl, 3,5-difluorophenyl, 2,4-difluorophenyl, and 2,5-difluorophenyl; more preferably phenyl, 3-fluorophenyl, 3-chlorophenyl, 3,5-difluorophenyl, 3,5-dichlorophenyl. Preferred pyridyl groups are 3-pyridyl; 5-bromo-3-pyridyl; 5,6-dichloro-3-pyridyl; 4-pyridyl; 2-fluoro-4-pyridyl; 2-chloro-4-pyridyl; 2-chloro-6-methyl-4-pyridyl; and 2,6-dichloro-4-pyridyl. More preferred are 2-chloro-4-pyridyl; 2-fluoro-4-pyridyl; and 2,6-dichloro-4-pyridyl. A preferred furyl group is 2-furyl. Preferred thienyl groups are 2-thienyl and 3-thienyl.

$R^3$ is an alkynyl or alkoxyalkyl group. Preferably, $R^3$ is a ($C_3$-$C_6$)alkynyl or a ($C_1$-$C_6$)alkoxy($C_1$-$C_6$)alkyl group, either of which may be optionally substituted with up to five halogens. Preferred ($C_3$-$C_6$)alkynyl groups are straight alkynyl groups, such as n-pentynyl, n-propynyl and n-butynyl. Another preferred character of alkynyls is that they be 2-alkynyls, more preferably prop-2-ynyl and but-2-ynyl. Preferred ($C_1$-$C_6$)alkoxy($C_1$-$C_6$)alkyls are ($C_1$-$C_2$)alkoxy($C_1$-$C_3$)alkyl, more preferably methoxymethyl or 2-methoxyethyl and most preferably methoxymethyl.

$R^5$- - - $R^6$ is a fused ring moiety bonded to the pyrimidine ring at the 5 and 6 positions containing two to five atoms in its link, each of such atoms independently selected from carbon, oxygen and sulfur. For the purposes herein, -$R^5$- - - $R^6$- can alternatively be termed the $R^5$-$R^6$ link. As an illustration of one example of what is intended, when the $R^5$-$R^6$ link is designated as the four atom link —$CH_2CH_2CH_2CH_2$—, the following structure is attained:

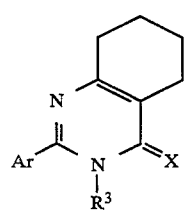

II

For instance, possible $R^5$-$R^6$ links are dimethylene (—$CH_2CH_2$—), trimethylene (—$CH_2CH_2CH_2$—), tetramethylene (—$CH_2CH_2CH_2CH_2$—) and pentamethylene (—$(CH_2)_5$—). Heteroatom substitution in the $R^5$-$R^6$ link using oxygen or sulfur can be present. Preferably at most only one oxygen or sulfur is used in the $R^5$-$R^6$ link when a heteroatom substitution is present. Examples are thioethylene (—$SCH_2CH_2$—) and oxyethylene (—$OCH_2CH_2$—). The $R^5$-$R^6$ link need not be a saturated link, but can contain double bonds. Examples are 1,3-butadienylene (—CH=CHCH=CH—) and thiovinylene (—SCH=CH—). The $R^5$-$R^6$ link can be a substituted link. For example, an ethyl substituent on the $R^5$-$R^6$ link can be present, such as in 1-ethyl-thiovinylene (—CH=C(CH$_2$CH$_3$)S—). Accordingly, embodiments of the invention can have one or more substituents independently selected from (C$_1$-C$_3$)alkyl groups, such as methyl, ethyl, and propyl, polyhalo(C$_1$-C$_3$)alkyl and halogen atoms as substituents on the $R^5$-$R^6$ link.

X is oxygen or sulfur, preferably oxygen.

A preferred embodiment of this invention are the compounds represented by formula I wherein X is oxygen and Ar is substituted or unsubstituted phenyl or pyridyl. When Ar is substituted, the substituents described hereinabove are used.

A more preferred embodiment of this invention are the compounds represented by formula I wherein X is oxygen; Ar is substituted or unsubstituted phenyl or substituted or unsubstituted pyridyl; and $R^3$ is (C$_3$-C$_6$) alkynyl. When Ar is substituted, the substituents described hereinabove are used.

A still more preferred embodiment of this invention is the compound represented by formula I wherein X is oxygen; Ar is substituted or unsubstituted phenyl or substituted or unsubstituted pyridyl; $R^3$ is (C$_3$-C$_6$) alkynyl; and the -$R^5$-$R^6$- link is composed of two, three or four carbon, and zero or one oxygen or sulfur atom. When Ar is substituted, the substituents described hereinabove are used.

Even more preferred is the compound represented by formula I wherein X is oxygen; Ar is phenyl, 3-substituted phenyl (i.e. meta-substituted phenyl), 3,5-disubstituted-phenyl or 2-substituted-4-pyridyl or 2,6-disubstituted-4-pyridyl; $R^3$ is propargyl; and the -$R^5$-$R^6$-link is —CH=CH—CH=CH—, or —S—CH=CH—, or —(CH$_2$)y— wherein y is 3 or 4. When Ar is substituted, the substituents described hereinabove are used.

A yet more preferred embodiment of this invention is the compound represented by formula I wherein X is oxygen; Ar is phenyl, 3-fluorophenyl, 3-chlorophenyl, 3,5-difluorophenyl, 3,5-dichlorophenyl, 2-chloro-4-pyridyl, 2-fluoro-4-pyridyl, or 2,6-dichloro-4-pyridyl; $R^3$ is propargyl; and the -$R^5$-$R^6$- link is —(CH$_2$)y— wherein y is 3 or 4.

Compounds encompassed by the present invention include, but are not limited to, those illustrated in Table 1. The synthesis methods (i.e., A, B, or C) specified in the table are described hereinafter in this specification. The sequence of letters in the "Synthesis" column indicates the relative sequence of steps performed. For instance, "B+A" indicates the steps of procedure B was first performed, followed by the steps of Procedure A.

TABLE 1

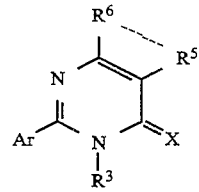

For the below table, S is sulfur, Et is ethyl, and for all compounds X = O (oxygen).

| Compound | Ar | $R^3$ | —$R^5$—$R^6$— | MP °C. | Synthesis |
|---|---|---|---|---|---|
| 1 | -Phenyl | —CH$_2$C≡CH | —CH$_2$CH$_2$CH$_2$— | 133–138 | B + A |
| 2 | -Phenyl | —CH$_2$C≡CH | —SCH=CH—* | 183–185 | C + A |
| 3 | -Phenyl | —CH$_2$C≡CH | —CH=C(Et)S—** | 115–117 | C + A |
| 4 | -2-Furyl | —CH$_2$C≡CH | —CH$_2$CH$_2$CH$_2$CH$_2$— | 112–114 | A |
| 5 | -Phenyl | —CH$_2$C≡CH | —CH=CHCH=CH— | 199–201 | C + A |
| 6 | -Phenyl | —CH$_2$C≡CH | —CH$_2$CH$_2$CH$_2$CH$_2$— | 137–141 | B + A |

*the sulfur atom (S) is bonded to the carbon atom at the 5 position of the pyrimidine ring
**the sulfur atom (S) is bonded to the carbon atom at the 6 position of the pyrimidine ring The 5,6-ring-fused pyrimidines of the present invention may be prepared by standard synthetic routes such as those illustrated below.

Method A—General Description

A precursor compound having the structure of formula I above with hydrogen (H) in the $R^3$ substituent position is selected. Reaction with $R^3Y$ is performed in a base-solvent mixture. Y can be a halogen, alkanesulfonate, haloalkanesulfonate or optionally substituted benzenesulfonate. The bases can be sodium hydride, alkali metal hydroxides, alkali metal carbonates or alkali metal alkoxides. The solvent can be alcohol, ketone, water, ether, DMSO or DMF. A mixture of N- and O-alkylated products results.

Method A—Specific Example 1—Preparation of 2-phenyl-3-propargyl-3,5,6,7-tetrahydro-4H-cyclopentapyrimidin-4-one. (Compound 1)

A slurry of 8.3 g (39.1 mmol) of 2-phenyl-3,5,6,7-tetrahydro-4H-cyclopentapyrimidin-4-one in 60 mL of tetrahydrofuran was added to 1.9 g (48 mmol) of 60% sodium hydride, with external cooling. A 6.4 g (43.0 mmol) portion of 80% by weight of propargyl bromide in toluene was added to the cooled solution. The ice bath was removed and the reaction was refluxed for 6 hours. The solvent was removed in vacuo, ether was added to the residue and the reaction was washed 3 times with water and once with brine. The organic layer was dried over MgSO4 and concentrated to yield 5.0 g of crude semisolid product. The crude product was dissolved in a small amount of methylene chloride and passed through a 6 inch plug of silica gel, washing with 1 of methylene chloride. The silica gel was washed further with 1 L of ether. The ether was removed in vacuo to yield 0.5 g (5.1%) of 2-phenyl-3-propargyl-3,5,6,7-tetrahydro-4H-cyclopentapyrimidin-4-one (Compound 1) as a white solid. $^1$H-NMR (CDCl$_3$) δ 2.15 (2H,m), 2.35 (1H,t), 2.95 (4H,t), 4.65 (2H,t), 7.55 (3H,m), 7.7 (2H,m).

Method A—Specific Example 2—Preparation of 2-phenyl-3-propargyl-[3,2-d]-thieno-4(3H)-pyrimidinone (Compound 2)

A mixture of 12.95 g (48.2 mmol) of 2-phenyl-[3,2-d]-thieno-4(3H)-pyrimidinone, 2.87 g (53.1 mmol) of sodium methoxide and 100 mL of methanol was heated to reflux. To the hot stirred slurry was added 7.59 g (50.9 mmol) of an 80% by weight solution of propargyl bromide in toluene. Refluxing was continued for 3.5 days. The bulk of the methanol was rotovapped off and the residue was partitioned between 150 mL of water and 150 mL of ethyl acetate. The mixture was filtered to remove unreacted 2-phenyl-[3,2-d]-thieno-4(3H)-pyrimidinone. The organic layer of the filtrate was separated and the aqueous layer was extracted with 100 mL of ethyl acetate. The combined organic extracts were washed with brine, dried over MgSO4 and concentrated to afford 3.03 g of a solid. This material was purified by flash chromatography on a column of 50 g of silica gel, eluting with 20, 30, 40, 50, 75 and 100% ether in hexanes to give 1.27 g of crude product. This crude product was taken up in 150 mL of ethyl acetate, washed with three 50 mL portions of 5% aqueous hydrochloric acid and 50 mL of saturated aqueous NaHCO3, and dried over MgSO4. Removal of the solvent left 0.89 g (7%) of 2-phenyl-3-propargyl-[3,2-d]-thieno-4(3H)-pyrimidinone (Compound 2) as an off-white solid, mp 183°-185° C. $^1$H-NMR (CDCl3) δ 2.35(1H,t), 4.7(2H,d), 7.35(1H,d), 7.55(3H), 7.7(1H,d).

Method B—General Description

An amidine hydrochloride or other salt is heated with a beta-keto ester in a solvent in the presence of a base to neutralize the hydrochloric acid. Solvents useable include xylene or toluene, preferably, or ethanol or heptane. Sodium acetate or sodium ethoxide can be the base:

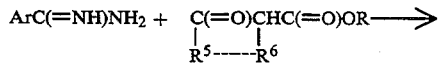

Figure I with $R^3$ = H; precursor for Method A

Method B—Specific Example

A mixture of 15.6 g (190 mmol) of sodium acetate, 25 mL (172.7 mmol) of ethyl cyclopentanone-2-carboxylate, 27.7 g (177 mmol) of benzamidine hydrochloride and 250 mL of xylene was refluxed with a Dean Stark trap for 8 hours. Most of the xylene was distilled off and the hot reaction mixture was poured onto crushed ice. The reaction mixture was left to stand at room temperature for 0.5 hour, then vacuum filtered to remove the product, as a gray solid. The solid was air dried overnight to yield 13.35 g (37.0%) of 2-phenyl-3,5,6,7-tetrahydro-4H-cyclopentapyrimidin-4-one. $^1$H-NMR (CDCl3) δ2.11 (2H,m), 2.90 (4H,m), 7.5 (3H,m), 8.18 (2H,m).

Method C—General Description

A 3-aroylaminoacrylamide derivative is cyclized with base to give a pyrimidinone. The starting material is prepared by acylation of the corresponding 3-aminoacrylamide or by acylation of a 3-aminoacrylate ester followed by ammonolysis:

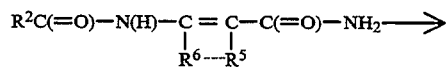

Figure I with $R^3$ =H;

Method C—Specific Examples—Preparation of 2-phenyl-[3,2-d]-thieno-4(3H)-pyrimidinone (a) A stirred solution of 1905 g (0.12 mol) of methyl 3-amino-2-thiophenecarboxylate and 12 mL of pyridine in 200 mL of dichloromethane was cooled in an ice bath and 15.5 mL (0.13 mol) of benzoyl chloride was added dropwise over 15 min. The mixture was stirred in the ice bath for 15 min and then at room temperature for 4 h. The solvent was removed on the rotovap and the residue was partitioned between 100 mL of 5% aqueous hydrochloric acid and three 100 mL portions of ether. The combined organic extracts were washed with 50 mL of 5% aqueous hydrochloric acid and 50 mL of saturated aqueous sodium bicarbonate, and dried over MgSO4. Removal of the solvent left 30.73 g (98%) of crude methyl 3-(benzoylamino)-2-thiophenecarboxylate. $^1$H-NMR (CDCl3) δ 3.90(3H,s), 7.50(4H,m), 8.00(2H,m), (b) To a stirred solution of 14.21 g (54.4 mmol) of crude methyl 3-(benzoylamino)-2-thiophenecarboxylate in 100 mL of methanol and 100 mL of THF was added 100 mL of concentrated aqueous ammonia. The mixture was stirred at room temperature for 5 days and an additional 100 mL of concentrated aqueous ammonia was added. After stirring for 5 more days the mixture was rotovapped to remove the bulk of the organic solvents and the residue was extracted with two 125 mL portions of ethyl acetate. The insoluble material was collected by filtration and combined with the residue from evaporating the ethyl acetate extracts to dryness to furnish 11.96 g (89%) of crude 3-(benzoylamino)-2-thiophenecarboxamide as a tan solid. $^1$H-NMR (d6-DMSO) δ 7.55(3H,m), 7.7(1H,d), 7.95(2H,m), 8.18(1H,d).

(c) A suspension of 11.85 g (48.2 mmol) of crude 3-(benzoylamino)-2-thiophenecarboxamide in 100 mL of 5% aqueous NaOH was refluxed for 0.5 h. The mixture was allowed to cool and neutralized by addition of conc HCl. The mixture was filtered and 12.95 g of wet 2-phenyl-[3,2-d]thieno-4(3H)-pyrimidinone was collected. This material was used without drying or purification. $^1$H-NMR (d6-DMSO) δ 7.45(1H,d), 7.55(3H,m), 8.18(3H,m).

Methods of Use

In another aspect, this invention relates to a method of controlling weeds comprising applying to said weed or the locus of said weed or to the surface of the growth medium of said weed a herbicidally effective amount of a compound of the formula:

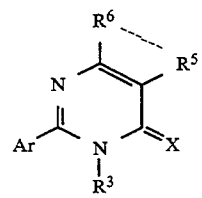

wherein Ar is an aryl or heteroaromatic group (e.g. aromatic ring structure having four to ten carbon atoms): $R^3$ is an alkynyl or alkoxyalkyl group; -$R^5$-$R^6$- is a two to five atom linking group composed of carbon, oxygen and sulfur that forms a ring fused to the 5- and 6- positions of the pyrimidine; and X is oxygen or sulfur. The particulars as to the substituents and preferences therefore are as stated hereinabove in the compound embodiments.

The compounds of the invention are useful as preemergence and postemergence herbicides. In general, they require lower doses to control weeds preemergence. Preemergence herbicides are usually applied to the soil either before, during or after seeding, but before the crop emerges. Postemergence herbicides are applied after the plants have emerged and during their growth period. The embodied materials generally show selectivity to several agronomically important crops such as corn, cotton, rice, soybean, sugarbeet, sunflower, peanut and wheat.

Under some conditions the compounds of the invention may be incorporated into the soil or other growth medium prior to planting a crop. This incorporation may be by arty convenient means, including mixing with the soil, applying the compound to the surface of the soil and then dishlug or dragging into the soil to the desired depth, or by employing a liquid carrier.

The 2-aryl-5,6-ring-fused pyrimidines of the present invention can be applied to various loci such as the soil or the foliage. For such purposes these compounds can be used in the technical or pure form as prepared, as solutions or as formulations. The compounds are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual," Allured Publishing Company, Ridgewood, N.J., U.S.A.

The 2-aryl-5,6-ring-fused pyrimidines can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 0.01 lb. to about 10 lbs. per acre of the active ingredient.

As a soil treatment the chemical can be incorporated in the soil or applied to the surface usually at a rate of from about 0.01 to about 10 lbs. per acre. As a foliar spray, the toxicant is usually applied to growing plants at a rate of from about 0.01 to about 10 lbs. per acre.

The 2-aryl-5,6-ring-fused pyrimidines of the invention can also be mixed with fertilizers or fertilizing materials before their application. In one type of solid fertilizing composition in which the 2-aryl-5,6-ring-fused pyrimidines can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The 2-aryl-5,6-ring-fused pyrimidine will commonly be from about 5% to about 25% of the fertilizing composition. These compositions provide fertilizing materials which promote the rapid growth of desired plants, and at the same time control the growth of undesired plants.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloro terephthalate;
trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester and
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2-yl)aminocarbonyl]-benzenesulfonamide;

3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1methylurea;
3-(4-chlorophenyl)-1-methoxy-1-methylurea;
3-(3,4-dichlorophenyl)-1,1,3-trimethylurea;
3-(3,4-dichlorophenyl)diethylurea;
dichloral urea;
methyl 2-[[[[(4,6-dimethyl-2-pyrimidinyl)amino]-carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[(4-methoxy-6-methyl-1,3,5-triazin-2-yl)aminocarbonyl]aminosulfonyl]-2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio )-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxy]-2-nitrobenzoate;
5-[2-chloro-4-(trifluoromethyl)phenoxyl]-N-(methylsulphonyl)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;
maleic hydrazide;
3-amino-1,2,4-triazole; monosodium methanearsonate;
disodium methanearsonate;
N,N-dimethyl-alpha,alpha-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid:
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6- tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-($\alpha,\alpha,\alpha$-trifluoro-m-toluyl)-3-(2H)-pyridazinone;
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired. The herbicidal activity of the 2-aryl-5,6-ring-fused pyrimidines of the present invention towards a number of common weeds was evaluated using a greenhouse method of testing. Using the procedures described below, the 2-aryl-5,6-ring-fused pyrimidines of the present invention were evaluated for control of weeds selected from the following:

| Monocots | |
|---|---|
| Barnyardgrass (BYG) | *Echinochloa crus-galli* |
| Crabgrass (CRB) | *Digitaria sanguinilis* |
| Foxtail (FOX) | *Setaria viridis* |
| Johnsongrass (JON) | *Sorghum halepense* |
| Meadow Foxtail (MF) | *Alopecurus pratensis* |
| Nutsedge (NUT) | *Cyperus esculentus* |
| Wild Oat (WO) | *Avena fatua* |
| Dicots | |
| Beggartick (BID) | *Bidens pilosa* |
| Cocklebur (CKL) | *Xanthium strumarium* |
| Morningglory (MG) | *Ipomoea lacunosa* |
| Nightshade (NS) | *Solanum nigrum* |
| Pigweed (PIG) | *Amaranthus retroflexus* |
| Smartweed (SMT) | *Polygonum lapathifolium* |
| Velvetleaf (VEL) | *Abutilon theophrasti* |

The following test procedure was employed. Seeds of selected plants were planted in flats or pots. For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants were selected for uniformity, size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 25 or 50 gallons per acre at the: rate of application in pounds per acre (LB/A) specified in the below tables. About two or three weeks after application of the test compound, the state of growth of the plant was observed. Each species was evaluated on a scale of 0–100 in which 0 equals no activity and 100 equals total control. The row heading abbreviations in the below tables for the plants tested are the same as for the moncots and dicots hereinabove. The dash ("-") entry signifies no testing for the specified conditions. The following tables show the results obtained for the test compounds at the stated rate of application and are provided merely as illustrations and are not to be considered as limitations or restrictions of the scope of this invention which is defined by the claims.

TABLE 2

| | Preemergence Application | | | | | |
|---|---|---|---|---|---|---|
| | Cmpd No. 1 | Cmpd No. 2 | Cmpd No. 3 | Cmpd No. 4 | Cmpd No. 5 | Cmpd No. 6 |
| LB/A | 4.00 | 2.00 | 1.00 | 1.00 | 1.00 | 1.00 |
| BID | — | — | 0 | 0 | 0 | 85 |
| CKL | 15 | — | — | — | — | — |
| MG | 100 | — | — | — | — | — |
| NS | — | 90 | 50 | 0 | — | 100 |
| PIG | 100 | — | — | — | — | — |
| SMT | 100 | 0 | 100 | 0 | — | 60 |
| VEL | 100 | 10 | 0 | 0 | 40 | 0 |
| BYG | 100 | 10 | 25 | 0 | 40 | 90 |
| CRB | — | — | 95 | 50 | 100 | 95 |
| FOX | 100 | 15 | 25 | 0 | 90 | 100 |
| JON | 100 | — | — | — | — | — |

TABLE 2-continued

| | Preemergence Application | | | | | |
|---|---|---|---|---|---|---|
| | Cmpd No. 1 | Cmpd No. 2 | Cmpd No. 3 | Cmpd No. 4 | Cmpd No. 5 | Cmpd No. 6 |
| MF | — | — | 0 | 0 | 0 | 100 |
| NUT | 80 | — | — | — | — | — |
| WO | 98 | 0 | — | — | — | — |

TABLE 3

| | Postemergence Application | | | | | |
|---|---|---|---|---|---|---|
| | Cmpd No. 1 | Cmpd No. 2 | Cmpd No. 3 | Cmpd No. 4 | Cmpd No. 5 | Cmpd No. 6 |
| LB/A | 4.00 | 2.00 | 1.00 | 1.00 | 1.00 | 1.00 |
| BID | — | — | 0 | 0 | 10 | 40 |
| CKL | 15 | — | — | — | — | — |
| MG | 35 | — | — | — | — | — |
| NS | — | 40 | 50 | 0 | 20 | 90 |
| PIG | 20 | 10 | — | — | — | — |
| SMT | 60 | 0 | 0 | 0 | 0 | 95 |
| VEL | 0 | 0 | 0 | 0 | 0 | 20 |
| BYG | 85 | 0 | 0 | 0 | 0 | 70 |
| CRB | — | — | 0 | 0 | 0 | 95 |
| FOX | 98 | 0 | 0 | 0 | 0 | 30 |
| JON | 40 | — | — | — | — | — |
| MF | — | — | 0 | 0 | 0 | 60 |
| NUT | 15 | — | — | — | — | — |
| WO | 20 | 0 | — | — | — | — |

It is to be understood that changes and variations may be made without departing from the spirit and scope of the invention as defined by the appended claims.

What is claimed is:

1. A compound of the formula

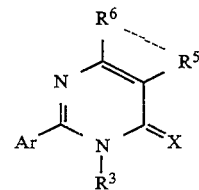

wherein (a) Ar is a furyl, phenyl, pyridyl, or thienyl group, each of said group is optionally substituted with up to three substituents independently selected from a bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_2)$alkyl, halo$(C_2-C_{12})$alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, carbo$(C_1-C_6)$alkoxy, or nitro group; and (b) $R^3$ is a $(C_3-C_6)$alkynyl or $(C_1-C_6)$alkoxy$(C_1-C_6)$alkyl, said $(C_3-C_6)$alkynyl group or $(C_1-C_6)$alkoxy$(C_1-C_6)$ alkyl group is optionally substituted with up to five halogens; and (c) -$R^5$ - - - $R^6$- is a saturated link moiety containing two to five atoms in its link, is bonded to the carbon atoms at the 5 and 6 position of the pyrimidine ring, and together with the carbon atoms at the 5 and 6 position forms a fused ring, each of said atoms being a carbon and the link atoms may be unsubstituted or substituted with one or more substituents independently selected from ($C_1-C_3$)alkyl groups polyhalo ($C_1-C_3$)alkyl groups and halogen atoms; and (d) X is oxygen or sulfur.

2. The compound of claim 1 wherein Ar is a phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 2-fluorophenyl, 3,5-dichlorophenyl, 3,5-difluorophenyl, 2,4-difluorophenyl, or 2,5-difluorophenyl, a 3-pyridyl, 5-bromo-3-pyridyl, 5,6-dichloro-3-pyridyl, 4-pyridyl, 2-fluoro-4-pyridyl, 2-chloro-4-pyridyl, or 2,6-dichloro-4-pyridyl, 2-furyl, 2-thienyl, or 3-thienyl group.

3. The compound of claim 1 wherein $R^3$ is a pentynyl, propynyl, butynyl, methoxymethyl or 2-methoxyethyl group.

4. The compound of claim 1 wherein -$R^5$ - - $R^6$- is made up of two, three, four or five substituted or unsubstituted methylene (—$CH_2$-) groups wherein said methylene carbons may be substituted with a ($C_1-C_3$)alkyl, polyhalo($C_1-C_3$)alkyl or halo groups.

5. The compound of claim 1 wherein X is oxygen and Ar is substituted or unsubstituted phenyl or pyridyl.

6. The compound of claim 5 wherein X is oxygen; Ar is substituted or unsubstituted phenyl or substituted or unsubstituted pyridyl; and $R^3$ is ($C_3-C_6$) alkynyl.

7. The compound of claim 6 wherein X is oxygen; Ar is phenyl, 3-substituted phenyl, 3,5-disubstituted phenyl, 2-substituted-4-pyridyl or 2,6-disubstituted-4-pyridyl; $R^3$ propargyl; and -$R^5$ - - - $R^6$- is —($CH_2$)y— wherein y is three or four.

8. The compound of claim 7 wherein X is oxygen; Ar is phenyl, 3-fluorophenyl, 3-chlorophenyl, 3,5-difluorophenyl, 3,5-dichlorophenyl, 2-chloro-4-pyridyl, 2-fluoro-4-pyridyl, or 2,6-dichloro-4-pyridyl; $R^3$ is propargyl; and $R^5$-$R^6$ is —$CH_2C_2CH_2$— or —$CH_2CH_2CH_2CH_2$—.

9. The compound of claim 1 wherein Ar is phenyl, $R^3$ is propargyl, and -$R^5$ - - - $R^6$- is selected from trimethylene and tetramethylene.

10. The compound of claim 1 wherein Ar is 2-furyl, $R^3$ is propargyl, and -$R^5$ - - - $R^6$- is tetramethylene.

11. A herbicidal composition comprising an agronomically acceptable carrier and a herbicidally effective amount of a compound of the formula:

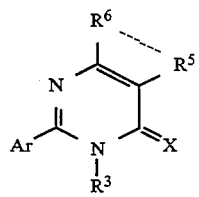

wherein (a) Ar is a furyl, phenyl, pyridyl, or thienyl group, each of said group is optionally substituted with up to three substituents independently selected from a bromo, chloro, fluoro, ($C_1-C_{12}$)alkyl, cyclo($C_3-C_8$)alkyl, ($C_2-C_{12}$)alkenyl, cyclo($C_3-C_8$)alkenyl, ($C_2-C_{12}$)alkynyl, halo($C_1-C_{12}$)alkyl, polyhalo($C_1-C_{12}$)alkyl, halo($C_2-C_{12}$)alkenyl, polyhalo($C_2-C_{12}$)alkenyl, halo($C_2-C_6$)alkynyl, polyhalo($C_2-C_6$)alkynyl, ($C_1-C_{12}$)alkoxy, ($C_1-C_{12}$)alkylthio, ($C_1-C_{12}$)alkylsulfonyl, ($C_1-C_{12}$)alkylsulfinyl, phenyl, phen($C_1-C_{12}$)alkyl, phen($C_2-C_{12}$)alkenyl, phen($C_2-C_{12}$)alkynyl, cyano, halo($C_1-C_{12}$)alkoxy, carbo($C_1-C_6$)alkoxy, or nitro group; and (b) $R^3$ is a ($C_3-C_6$)alkynyl or ($C_1-C_6$)alkoxy($C_1-C_6$)alkyl, said ($C_3-C_6$)alkynyl group or ($C_1-C_6$) alkoxy ($C_1-C_6$) alkyl group is optionally substituted with up to five halogens; and (c) -$R^5$ - - - $R^6$- is a unsaturated and saturated link moiety containing two to five atoms in its link, is bonded to the carbon atoms at the 5 and 6 position of the pyrimidine ring, and together with the carbon atoms at the 5 and 6 position forms a fused ring, each of said atoms being a carbon and the link atoms may be unsubstituted or substituted with one or more substituents independently selected from ($C_1-C_3$)alkyl groups, polyhalo ($C_1-C_3$)alkyl groups and halogen atoms; and (d) X is oxygen or sulfur.

12. A method of controlling a weed comprising applying to the locus of said weed or to the growth medium of said weed a herbicidally effective amount of a compound of the formula:

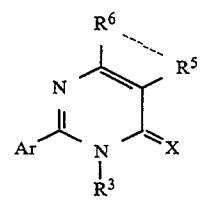

wherein (a) Ar is a furyl, phenyl, pyridyl, or thienyl group, each of said group is optionally substituted with up to three substituents independently selected from a bromo, chloro, fluoro, ($C_1-C_{12}$)alkyl, cyclo($C_3-C_8$)alkyl, ($C_2-C_{12}$)alkenyl, cyclo($C_3-C_8$)alkenyl, ($C_2-C_{12}$)alkynyl, halo($C_1-C_{12}$)alkyl, polyhalo($C_1-C_{12}$)alkyl, halo($C_2-C_{12}$)alkenyl, polyhalo($C_2-C_{12}$)alkenyl, halo($C_2-C_6$)alkynyl, polyhalo($C_2-C_6$)alkynyl, ($C_1-C_{12}$)alkoxy, ($C_1-C_{12}$)alkylthio, ($C_1-C_{12}$)alkylsulfonyl, ($C_1-C_{12}$)alkylsulfinyl, phenyl, phen($C_1-C_{12}$)alkyl, phen($C_2-C_2$)alkenyl, phen($C_2-C_{12}$)alkynyl, cyano, halo($C_1-C_{12}$)alkoxy, carbo($C_1-C_6$)alkoxy, or nitro group; and (b) $R^3$ is a ($C_3-C_6$)alkynyl or ($C_1-C_6$)alkoxy($C_1-C_6$)alkyl, said ($C_3-C_6$)alkynyl group or ($C_1-C_6$) alkoxy ($C_1-C_6$) alkyl group is optionally substituted with up to five halogens; and (c) -$R^5$ - - - $R^6$- is a unsaturated or saturated link moiety containing two to five atones in its link, is bonded to the carbon atoms at the 5 and 6 position of the pyrimidine ring, and together with the carbon atoms at the 5 and 6 position forms a fused ring, each of said atoms being a carbon and the link atoms may be unsubstituted or substituted with one or more substituents independently selected from ($C_1-C_3$)alkyl groups, polyhalo ($C_1-C_3$)alkyl groups and halogen atoms; and (d) X is oxygen or sulfur.

* * * * *